US00PP12104P2

(12) United States Plant Patent
Miyazaki

(10) Patent No.: US PP12,104 P2
(45) Date of Patent: Sep. 25, 2001

(54) SENECIO GENUS PLANT NAMED 'SUNSENEBU'

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/347,224

(22) Filed: Jul. 2, 1999

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

A new variety of Senecio plant is provided that forms clusters of attractive large single flowers having violet petals with no marginal variegation and dark violet disks. A tall growth habit with abundant branching is displayed. The stems possess sparse pubescence. The flowering duration is long and the flowers posses some fragrance.

2 Drawing Sheets

BACKGROUND OF THE VARIETY

The present invention relates to a new and distinct variety of Senecio plant named 'Sunsenebu'. 'Sunsenebu' is a distinct and unique variety, which displays a tall dome-shaped growth habit with abundant branching, vivid violet flowers, and a long blooming period.

There are many varieties in *Senecio L. Senecio cruentus* commonly is known as Cineraria and is cultivated in many parts of the world. There are many cultivated varieties having a single flower color of white, pink, red, blue or violet. Some varieties have marginal color variegation.

The female parent used in the crossing of 'Sunsenebu' is the, *Senecio cruentus*, 'Jupiter Blue' variety (non-patented in the United States and not commercially available in the United States). 'Jupiter Blue' is a compact dome-shaped plant having a height of approximately, 18.5 cm. The stems are thick, and 8.3 mm in diameter with anthocyanin coloration. The leaves are of a serrated heart-shaped form and are grayish yellow green in coloration. The leaf size is medium, 12.0 cm in length and 12.5 cm in width. The flower is single and has vivid blue petals with a deep blue flower disk and no marginal variegation. 'Jupiter Blue' has some fragrance.

The pollen parent used in the crossing of 'Sunsenebu' is an unnamed variety of *Senecio heritierii* (non-patented in the United States and not commercially available in the United States), which was introduced from nursery in England. *Senecio heritierii* is recognized to be a tall dome-shaped plant that is approximately 26 cm in height with abundant branching. Stems are 5.1 mm in diameter with no anthocyanin coloration. The leaves are serrated heart-shaped and are light yellowish green in coloration. The leaf size is small, 5.5 cm in length and 6.3 cm in width. Flowers are single with strong purple petals with some white parts and strong reddish purple disk flowers. *Senecio heritierii* has no fragrance.

The controlled crossing with *Senecio cruentus* 'Jupiter Blue' and *Senecio heritierii* was conducted at the Hakushu Research Center located at Hakushu-cho, Kitakoma-gun, Yamanashi-ken, Japan in January 1995. Seedlings from this crossing were produced. The new variety of the present invention was selected in January 1996 in view of the flower coloration and early blooming. After asexual propagation by tissue culture and the use of cuttings at the same location, the botanical characteristics of the selected variety were examined and were tested using parental varieties and the 'Miss Yokohama', and 'Midget' varieties, for comparative purposes beginning in July 1996. As a result, it is confirmed that this selected variety of the present invention is distinctive and uniform and stable in its characteristics.

The new variety of Senecio genus plant was named 'Sunsenebu' and is botanically classified (*Senecio cruentus*× *Senecio heritierii*).

In the following description, the color-coding is in accordance with the R.H.S. Colour Chart of The Royal Horticultural Society, London, England. The color chart based on The Japan Color Standard for Horticultural Plants (J.H.S. Color Chart) is also added for reference.

The botanical characteristics of the female parent plant *Senecio cruentus*, 'Jupiter Blue' used in the crossing of 'Sunsenebu' are as follows:

Plant:
- *Growth habit.*—Dwarf compact.
- *Height.*—18.5 cm.

Stem:
- *Thickness.*—8.3 mm.
- *Color.*—Moderate yellow green (RHS 139C, J.H.S. 3709).
- *Anthocyanin coloration.*—Present.
- *Degree of anthocyanin coloration.*—Moderate.
- *Branching.*—Slight.
- *Type of primary lateral shoot.*—Branch from every node.
- *Pubescence.*—Sparse.
- *Length of internode.*—0.5 cm.

Flower (single flowered):
- *Whole shape.*—Heart-shaped.
- *Depth of convexity of leaf margin.*—Shallow.
- *Type of convexity.*—Rounded.
- *Apex shape.*—Obtuse.
- *Base shape.*—Cordate.
- *Degree of undulation.*—Moderate.
- *Length.*—12.0 cm.
- *Width.*—12.5 cm.
- *Diameter of petiole.*—5.8 mm.

*Length of petiole.*—6.0 cm.
*Stipule.*—Absent.
*Color of upper surface.*—Grayish yellow green (RHS 38B, J.H.S. 3715).
*Color of reverse surface.*—Moderate yellow green (RHS 138D, J.H.S. 3702).
*Anthocyanin coloration of reverse surface.*—Present.
*Degree of anthocyanin coloration.*—Moderate.
*Pubescence of upper surface.*—Present.
*Pubescence of reverse surface.*—Dense.
*Color of pubescence of reverse surface.*—White.
*Shape of flower cluster.*—Flat.
*Diameter of flower cluster.*—20 cm.
*Height of flower cluster.*—10 cm.
*Cross-sectional shape of corolla.*—Reflexed.
*Diameter of flower.*—5.6 cm.
*Size of flower disk.*—1.8 cm.
*Color of petals.*—Vivid blue (RHS 100A, J.H.S. 7605).
*Marginal variegation.*—Absent.
*Color of flower disk.*—Deep blue (RHS 99B, J.H.S. 7606).
*Petal length.*—1.9 cm.
*Petal width.*—1.0 cm.
*Shape of petal.*—Generally rectangular.
*Lengthwise warp of petal.*—Convex.
*Concavity of petal tip.*—Present.
*Shape of petal tip.*—Flattened.
*Number of ray flowers.*—13.
*Number of disk flowers.*—110.
*Diameter of pedicel of the first flower.*—1.6 mm.
*Length of pedicel of the first flower.*—2.5 cm.
*Number of flowers per flower cluster.*—63.
*Fragrance.*—Present.

Calyx:
*Degree of concavity.*—Moderate.
*Degree of recurvature.*—2.5 mm.
*Color.*—Very pale green (RHS 130D, J.H.S. 4302).
*Anthocyanin coloration.*—Absent.

Pistil:
*Color.*—Deep blue (RHS 99B, J.H.S. 7606).
*Number.*—1.
*Style.*—The style divides into two segments at the tip that are truncated.

Stamen:
*Color.*—Deep blue (RHS 99B, J.H.S. 7606).
*Type.*—The five anthers are connate and the filaments are separated.
*Blooming period.*—December following propagation in August.

Hardiness:
*Cold.*—Good.
*Rain.*—Good.
*Heat.*—Good.

Resistance:
*Disease.*—Good.
*Insects.*—Good.

The botanical characteristics of the male parent plant *Senecio heritierii* (unnamed seedling) used in the crossing of 'Sunsenebu' are as follows:

Plant:
*Growth habit.*—Semi-dwarf erect.
*Height.*—26 cm.

Stem:
*Thickness.*—5.1 mm.
*Color.*—Very pale green (RHS 128D, J.H.S. 4902).
*Anthocyanin coloration.*—Absent.
*Branching.*—Abundant.
*Type of primary lateral shoot.*—Branching occurs from every node.
*Pubescence.*—Dense.
*Length of internode.*—0.8 cm.

Leaf:
*Shape.*—Heart-shaped with a swollen basal part which is notched where the basal part of the leaf attaches to the petiole.
*Depth of concavity of leaf margin.*—Medium.
*Type of convexity.*—Acute with pointed serrations at the leaf margin.
*Apex shape.*—Obtuse.
*Base shape.*—Cordate.
*Degree of undulation.*—Weak.
*Length.*—5.5 cm.
*Width.*—6.3 cm.
*Diameter of petiole.*—3.5 mm.
*Length of petiole.*—7.5 cm.
*Stipule.*—Absent.
*Color of upper surface.*—Light yellowish green (RHS 136D, J.H.S. 4002).
*Color of reverse surface.*—Very pale green (RHS 128D, J.H.S. 4902).
*Anthocyanin coloration of reverse surface.*—Absent.
*Pubescence of upper surface.*—Dense.
*Pubescence of reverse surface.*—Dense.
*Color of pubescence of reverse surface.*—White.

Flower (single flowered):
*Shape of flower cluster.*—Uneven.
*Diameter of flower cluster.*—18 cm.
*Height of flower cluster.*—15 cm.
*Cross-sectional shape of corolla.*—Flat.
*Diameter of flower.*—4.8 cm.
*Size of flower disk.*—0.9 cm.
*Color of petal.*—Strong purple (RHS 81B, J.H.S. 8605).
*Marginal variegation.*—Present.
*Diameter of off color part.*—1.3 cm.
*Border of marginal variegation.*—Indistinct.
*Color of flower disk.*—Strong reddish purple (RHS 72A, J.H.S. 9214).
*Petal length.*—2.2 cm.
*Petal width.*—0.4 cm.
*Shape of petal.*—Generally rectangular.
*Lengthwise warp of petal.*—Flat.
*Concavity of petal tip.*—Present.
*Shape of petal tip.*—Acute.
*Number of ray flowers.*—13.
*Number of disk flowers.*—110.
*Diameter of pedicel of the first flower.*—1.2 mm.
*Length of pedicel of the first flower.*—2.5 cm.
*Number of flowers per flower cluster.*—35.
*Fragrance.*—Absent.

Calyx:
*Degree of concavity.*—Flat.
*Degree of recurvature.*—3.1 mm.
*Color.*—Very pale green (RHS 128D, J.H.S. 4902).
*Anthocyanin coloration.*—Present.

Pistil:
*Color.*—Strong reddish purple (RHS 72A, J.H.S. 9214).
*Number.*—1.
*Style.*—The style divides into two segments at the tip that are truncated.

Stamen:
*Color.*—Strong reddish purple (RHS 72A, J.H.S. 9214).
*Type.*—The five anthers are connate and the filaments are separated.
*Blooming period.*—End of January following propagation in August.
Hardiness:
*Cold.*—Good.
*Rain.*—Good.
*Heat.*—Good.
Resistance:
*Disease.*—Good.
*Insects.*—Good.

The botanical characteristics of the similar variety 'Miss Yokohama' variety (non-patented in the United States and not commercially available in the United States) for comparative purposes are as follows:

Plant:
*Growth habit.*—Dwarf compact.
*Height.*—19 cm.
*Spread.*—19 cm.
Stem:
*Thickness.*—5.4 mm.
*Color.*—Moderate yellow green (RHS 139C, J.H.S. 3709).
*Anthocyanin coloration.*—Present.
*Degree of anthocyanin coloration.*—Medium.
*Branching.*—Fair.
*Type of primary lateral shoot.*—Branching occurs from every node.
*Pubescence.*—Dense.
*Length of internode.*—0.5 cm.
Leaf:
*Shape.*—Heart-shaped with a swollen basal part which is notched where the basal part of the leaf attaches to the petiole.
*Depth of concavity of leaf margin.*—Medium.
*Type of convexity.*—Acute with pointed serrations at the leaf margin.
*Size of wings* (*swollen basal part*).—Large.
*Apex shape.*—Medium.
*Base shape.*—Cordate.
*Degree of undulation.*—Weak.
*Length.*—17.5 cm.
*Width.*—13.0 cm.
*Diameter of petiole.*—5.2 mm.
*Length of petiole.*—7.7 cm.
*Stipule.*—Present.
*Color of upper surface.*—Moderate yellow green (RHS 137C, J.H.S. 3712).
*Color of reverse surface.*—Moderate yellow green (RHS 138C, J.H.S. 3709).
*Anthocyanin coloration of reverse surface.*—Present.
*Degree of anthocyanin coloration.*—Medium.
*Pubescence of upper surface.*—Dense.
*Pubescence of reverse surface.*—Dense.
*Color of pubescence of reverse surface.*—White.
Flower (single flowered):
*Shape of flower cluster.*—Rounded.
*Diameter of flower cluster.*—23 cm.
*Height of flower cluster.*—17 cm.
*Cross-sectional shape of corolla.*—Flat.
*Diameter of flower.*—4.2 cm.
*Size of flower disk.*—1.1 cm.
*Color of petals.*—Vivid violet (RHS 96A, J.H.S. 8005).
*Marginal variegation.*—Present.
*Diameter of off color part.*—2.5 cm.
*Border of marginal variegation.*—Fairly clear.
*Color of disk flowers.*—Deep violet (RHS 93A, J.H.S. 8006).
*Petal length.*—1.6 cm.
*Petal width.*—0.8 cm.
*Shape of petal.*—Generally rectangular.
*Lengthwise warp of petal.*—Convex.
*Concavity of petal tip.*—Present.
*Shape of petal tip.*—Rounded.
*Number of ray flowers.*—13.
*Number of disk flowers.*—86.
*Diameter of pedicel of the first flower.*—1.7 mm.
*Length of pedicel of the first flower.*—2.7 cm.
*Number of flowers per flower cluster.*—90.
*Fragrance.*—Present.
Calyx:
*Degree of concavity.*—Flat.
*Degree of recurvature.*—1.2 mm.
*Color.*—Very pale green (RHS 130D, J.H.S. 4302).
*Anthocyanin coloration.*—Absent.
Pistil:
*Color.*—Deep violet (RHS 93A, J.H.S. 8006).
*Number.*—1.
*Style.*—The style divides into two segments at the tip that are truncated.
Stamen:
*Color.*—Deep violet (RHS 93A, J.H.S. 8006).
*Type.*—The five anthers are connate and the filaments are separated.
*Blooming period.*—January following propagation in August.
Hardiness:
*Cold.*—Good.
*Rain.*—Good.
*Heat.*—Good.
Resistance:
*Disease.*—Good.
*Insects.*—Good.

The botanical characteristics of the similar variety 'Midget' variety (non-patented and not commercially available in the United States) for comparative purposes are as follows:

Plant:
*Growth habit.*—Dwarf.
*Height.*—14 cm.
Stem:
*Thickness.*—5.6 mm.
*Color.*—Moderate yellow green (RHS 139C, J.H.S. 3709).
*Anthocyanin coloration.*—Present.
*Degree of anthocyanin coloration.*—Moderate.
*Branching.*—Fair.
*Type of primary lateral shoot.*—Branching occurs from every node.
*Pubescence.*—Dense.
*Length of internode.*—0.5 cm.
Leaf:
*Shape.*—Heart-shaped with a swollen basal part which is notched where the basal part of the leaf attaches to the petiole.
*Depth of concavity of leaf margin.*—Medium.

*Type of convexity.*—Acute with pointed serrations at leaf margin.
*Apex shape.*—Acute.
*Base shape.*—Cordate.
*Degree of undulation.*—Fair.
*Length.*—13.9 cm.
*Width.*—10.3 cm.
*Diameter of petiole.*—4.2 mm.
*Length of petiole.*—4.7 cm.
*Stipule.*—Present.
*Color of upper surface.*—Grayish yellow green (RHS 138A, J.H.S. 3514).
*Color of reverse surface.*—Grayish yellow green (RHS 138B, J.H.S. 3715).
*Anthocyanin coloration of reverse surface.*—Absent.
*Pubescence of upper surface.*—Present.
*Pubescence of reverse surface.*—Dense.
*Color of pubescence of reverse surface.*—White.

Flower (single flowered):
*Shape of flower cluster.*—Flat.
*Diameter of flower cluster.*—22 cm.
*Height of flower cluster.*—8 cm.
*Cross-sectional shape of corolla.*—Fairly closed.
*Diameter of flower.*—3.2 cm.
*Size of flower disk.*—0.8 cm.
*Color of petals.*—Vivid reddish purple (RHS 74A, J.H.S. 9207).
*Marginal variegation.*—Absent.
*Color of flower disk.*—Strong reddish purple (RHS 72A, J.H.S. 9209).
*Petal length.*—1.5 cm.
*Petal width.*—0.8 cm.
*Shape of petal.*—Elliptical.
*Lengthwise warp of petal.*—Flat.
*Concavity of petal tip.*—Present.
*Shape of petal tip.*—Acute.
*Number of ray flowers.*—13.
*Number of disk flowers.*—86.
*Diameter of pedicel of the first flower.*—1.5 mm.
*Length of pedicel of the first flower.*—2.5 cm.
*Number of flowers per flower cluster.*—180.
*Fragrance.*—Present.

Calyx:
*Degree of concavity.*—Flat.
*Degree of recurvature.*—2.2 mm.
*Color.*—Moderate yellow green (RHS 139C, J.H.S. 3709).
*Anthocyanin coloration.*—Absent.

Pistil:
*Color.*—Strong reddish purple (RHS 72A, J.H.S. 9209).
*Number.*—1.
*Style.*—The style divides into two segments at the tip that are truncated.

Stamen:
*Color.*—Strong reddish purple (RHS 72A, J.H.S. 9209).
*Type.*—The five anthers are connate and the filaments are separated.
*Blooming period.*—January following propagation in August.

Hardiness:
*Cold.*—Good.
*Rain.*—Good.
*Heat.*—Good.

Resistance:
*Disease.*—Good.
*Insects.*—Good.

SUMMARY OF THE VARIETY

The 'Sunsenebu' plants as well as the other plants described herein were propagated from cuttings in July and were observed during the following January. Such plants were grown in 15 cm pots in a greenhouse where the lowest winter temperature was controlled at 12° C.

'Sunsenebu' is a relatively tall dome-shaped plant averaging 33 cm in height at the blooming period. There is a branch from every node and branching is abundant. The stems are approximately 4.5 mm in diameter with light anthocyanin coloration and sparse pubescence.

The leaves are small and are approximately 6.7 cm in length and approximately 8.0 cm in width. The leaves are serrated heart-shaped with small swollen lobes at the basal part where attached to the petiole. The leaf coloration is moderate yellow green with light anthocyanin coloration on the reverse side. Pubescence on both sides of the leaves is dense. The petiole is approximately 7.4 cm in length and approximately 3.1 mm in diameter.

The flower cluster is large, generally above the leaves, and uneven in configuration (i.e., the individual flower heights are somewhat random in appearance). The flower is single with no marginal variegation. When the flower is completely open the petals slant downward. The flower diameter is 7.7 cm. The petals are 32 mm in length and 0.8 cm in width, and their coloration is vivid violet. The flower disk is 13 mm in diameter and the coloration is deep violet. A blossom typically has 13 to 15 ray flowers and 135 disk flowers. Approximately 65 flowers commonly are present in a flower cluster. The degree of recurvature of calyx is 1.0 mm. The calyx is concave and possesses some anthocyanin coloration. The pedicel is 5.1 cm length, and 1.0 mm in diameter. Flowers typically possess some fragrance.

The blooming period is early and of long duration. Flower buds grow one after another from an axil. Blooming commonly beings during the first ten days of December at Hakushu-cho, Kitakoma-gun, Yamanashi-ken, Japan and the blooming continues until May. An individual bloom commonly lasts approximately two weeks at temperatures of approximatley 15° C. The flower petals are not self-cleaning and commonly remain attached to the fully mature flowers.

The new variety possesses moderate cold hardiness and resistance to heat.

Its fertility is low, and 'Sunsenebu' forms no viable seeds. Sometimes a seed coat is formed that lacks an embryo.

The new 'Sunsenebu' variety can be readily distinguished from the varieties, 'Miss Yokohama' and 'Midget' and the parents *Senecio heritierii* and 'Jupiter Blue' in the following areas:

1. 'Sunsenebu' is a tall plant, commonly 33 cm in height. 'Miss Yokohama' is a compact plant having a height of 19 cm. 'Midget' is a compact plant having a height of 14 cm. The pollen parent *Senecio heritierii* is a semi-compact plant having a height of 26 cm and female parent 'Jupiter Blue' is a compact plant having a height of 18.5 cm.

2. The blossoms of 'Sunsenebu' have vivid violet petals, and deep violet disk flowers and no marginal variegation. Those of 'Miss Yokohama' have vivid violet petals and deep violet disk flowers and white margins. Those of 'Midget' have vivid reddish purple petals with strong reddish purple disk flowers and no marginal variegation. Those of female parent 'Jupiter Blue' have vivid blue petals, deep blue disk flowers and no marginal variegation. Those of pollen parent,

*Senecio heritierii*, have strong purple petals, strong reddish purple disk flowers and white margins.

3. The leaves of 'Sunsenebu' are smaller than those of the 'Miss Yokohama' and 'Midget' varieties.

4. The 'Sunsenebu' variety has lesser pubescence on the stems than the 'Miss Yokohama' and 'Midget' varieties.

5. The blooming period for the 'Sunsenebu' variety is longer than that of 'Miss Yokohama' and 'Midget' varieties.

6. The fertility of the 'Sunsenebu' variety is less than that of 'Miss Yokohama' and 'Midget' varieties.

Plant height, flower color and leaf size are the primary distinguishing characteristics of the new 'Sunsenebu' variety.

BRIEF DESCRIPTION OF THE PHOTOGRAPHS

DESCRIPTION OF THE VARIETY

Figure 1:
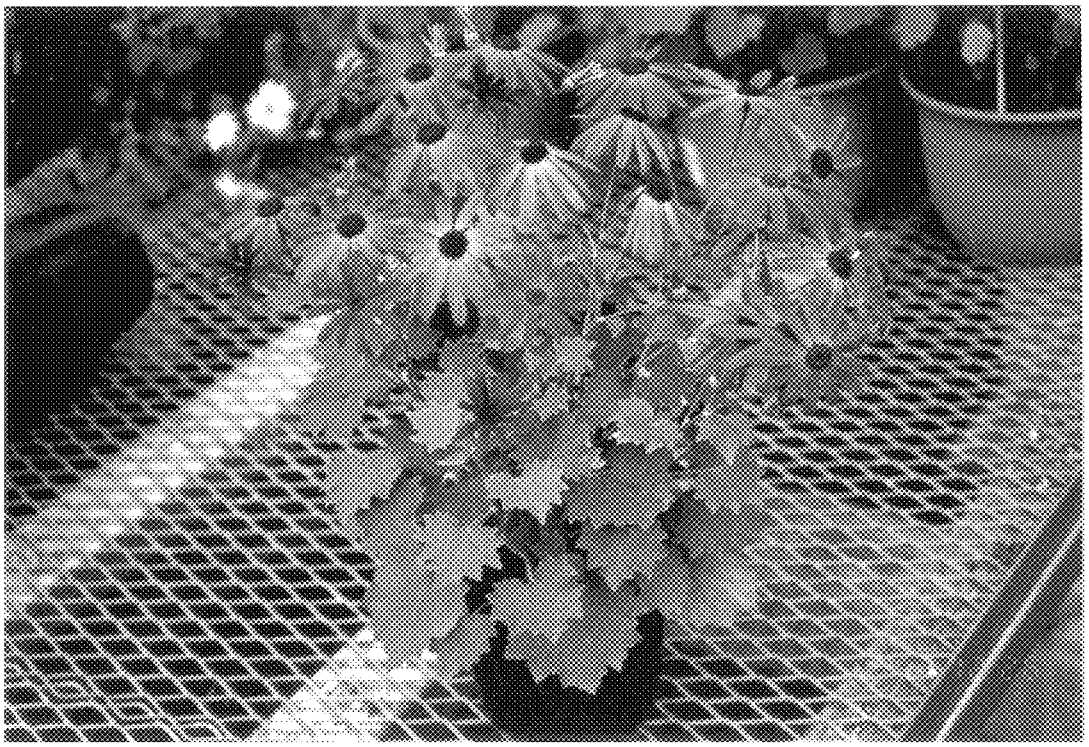
FIG. 1 depicts the overall growth habit of a typical potted plant of 'Sunsenebu' variety.
Figure 2:
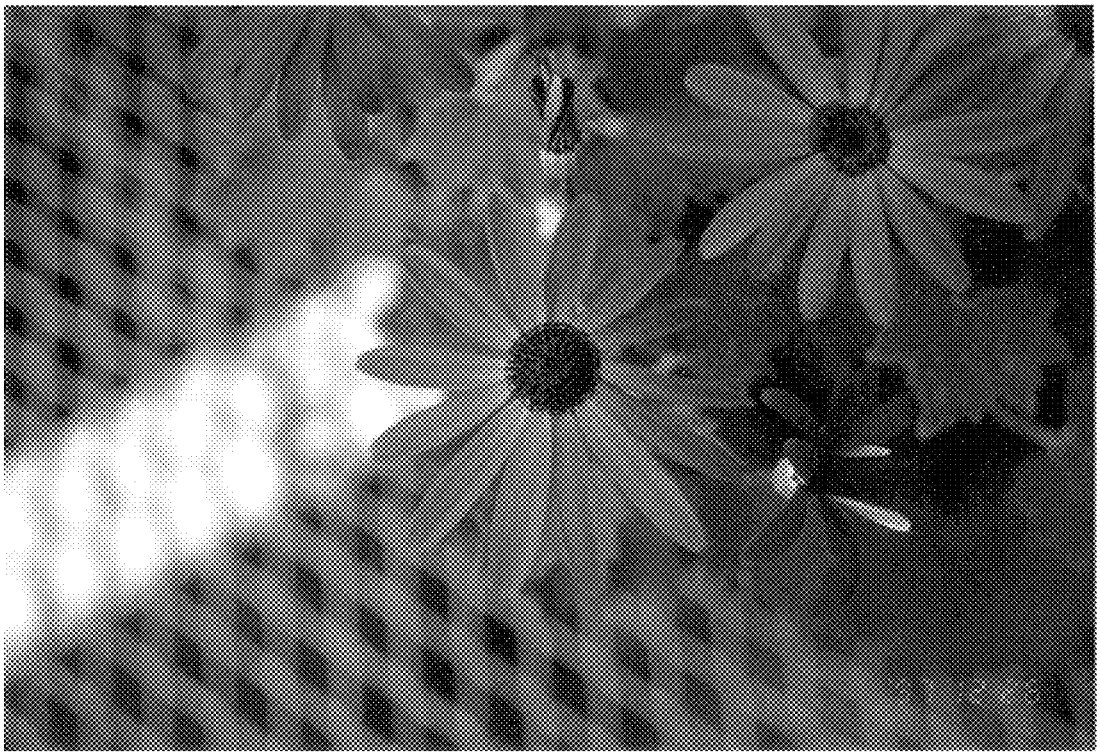
FIG. 2 depicts a close view of typical flowers of the 'Sunsenebu' variety. The coloration of the petals in the photographs appears to be slightly more reddish than the actual coloration.

The botanical characteristics of this new and distinct variety of Senecio genus plant named 'Sunsenebu' are as follows:

Plant:
- *Growth habit.*—Semi-erect.
- *Height.*—33 cm.

Stem:
- *Thickness.*—4.5 mm.
- *Color.*—Very pale green (RHS 147C).
- *Anthocyanin coloration.*—Present unevenly, and near RHS 165A where darkest and appears lighter where pubescence is present.
- *Branching.*—Abundant, commonly 9 to 11 branches per stem.
- *Type of primary lateral shoot.*—Branching occurs from every node.
- *Pubescence.*—Sparse.
- *Length of internode.*—1.4 cm.

Leaf:
- *Shape.*—Heart-shaped with a swollen basal part which is notched where the leaf attaches to the petiole.
- *Depth of concavity of leaf margin.*—Approximately 7 mm on average.
- *Type of convexity.*—Acute with pointed serrations at the leaf margin.
- *Apex shape.*—Acute.
- *Base shape.*—Cordate.
- *Degree of undulation.*—Weak.
- *Length.*—6.7 cm.
- *Width.*—8.0 cm.
- *Color of petiole.*—RHS 138B changing to RHS 59B at the base.
- *Diameter of petiole.*—3.1 mm.
- *Length of petiole.*—7.4 cm.
- *Stipule.*—Absent.
- *Color of upper surface.*—Moderate yellow green (RHS 137C, J.H.S. 3712).
- *Color of reverse surface.*—Moderate yellow green (RHS 138C, J.H.S. 3709).
- *Pubescence of upper surface.*—Dense.
- *Pubescence of reverse surface.*—Dense.
- *Color of pubescence of reverse surface.*—White.

Flower (single flowered):
- *Shape of flower cluster.*—Uneven with the respective flower heights of a cluster being somewhat random in appearance.
- *Diameter of flower cluster.*—36 cm.
- *Height of flower cluster.*—18 cm (the height of the upper most flower in a flower cluster minus the height of the lowest flower in the same flower cluster).
- *Cross-sectional shape of corolla.*—The petals slant downward when the flower is completely open.
- *Diameter of flower.*—7.7 cm.
- *Size of disk flower.*—1.3 cm.
- *Color of petals.*—Vivid violet (RHS 89C).
- *Marginal variegation.*—Absent (there is no change in coloration at the margin).
- *Color of flower disk.*—Deep violet (RHS 93A, J.H.S. 8006).
- *Petal length.*—3.2 cm.
- *Petal width.*—0.8 cm.
- *Shape of petal.*—Generally rectangular.
- *Lengthwise warp of petal.*—Flat.
- *Concavity of petal tip.*—Present.
- *Shape of petal tip.*—Acute.
- *Number of ray flowers.*—13 to 15.
- *Number of disk flowers.*—135.
- *Diameter of pedicel of the first flower.*—1.0 mm.
- *Length of pedicel of the first flower.*—5.1 cm.
- *Number of flowers per flower cluster.*—65.
- *Fragrance.*—Present.

Calyx:
- *Degree of concavity.*—Moderate.
- *Degree of recurvature.*—1.0 mm.
- *Color.*—Very pale green (RHS 130D, J.H.S. 4302).

Pistil:
- *Color.*—Deep violet (RHS 93A, J.H.S. 8006).
- *Number.*—1.
- *Style.*—The style divides into two segments at the tip that are truncated.

Stamen:
- *Color.*—Deep violet (RHS 93A, J.H.S. 8006).
- *Type.*—The five anthers are connate and the filaments are separated.
- *Blooming period.*—Beginning of December (following propagation in July).

Hardiness:
- *Cold.*—Good (can survive temperatures of 0° C.).
- *Heat.*—Good (withstands hot seasons at the indicated location).

Resistance:
- *Disease.*—Good with respect to Powdery Mildew and Leaf Spot).
- *Insects.*—Good with respect to Aphids, Whiteflies, and Thrips.).

The new 'Sunsenebu' is particularly well suited for growing as attractive ornamentation in pots.

I claim:

1. A new and distinct variety of Senecio plant named 'Sunsenebu', substantially as herein illustrated and described, having (A) a tall dome-shaped growth habit with abundant branching, (B) sparse pubescence on the stems, (C) small leaves, (D) clusters of large flowers having violet petals with no marginal variegation and deep violet disks, and (E) a long flowering period.

* * * * *